(12) United States Patent
Kreh et al.

(10) Patent No.: US 7,307,713 B2
(45) Date of Patent: Dec. 11, 2007

(54) APPARATUS AND METHOD FOR INSPECTION OF A WAFER

(75) Inventors: Albert Kreh, Solms (DE); Henning Backhauss, Wetzlar (DE)

(73) Assignee: Vistec Semiconductor Systems GmbH, Weilburg (DE)

( * ) Notice: Subject to any disclaimer, the term of this patent is extended or adjusted under 35 U.S.C. 154(b) by 387 days.

(21) Appl. No.: 11/011,095

(22) Filed: Dec. 15, 2004

(65) Prior Publication Data

US 2005/0134846 A1 Jun. 23, 2005

(30) Foreign Application Priority Data

Dec. 19, 2003 (DE) ............................... 103 59 723

(51) Int. Cl.
*G01N 21/00* (2006.01)
(52) U.S. Cl. ................. 356/237.2; 356/601; 250/458.1
(58) Field of Classification Search .. 356/327.1–327.5, 356/600–601; 250/559.41, 559.45, 216, 250/208.1
See application file for complete search history.

(56) References Cited

U.S. PATENT DOCUMENTS

| 4,305,658 | A | * | 12/1981 | Yoshida | 356/23 |
| 4,816,686 | A | * | 3/1989 | Hara et al. | 250/458.1 |
| 5,153,668 | A | * | 10/1992 | Katzir et al. | 356/237.2 |
| 5,892,579 | A | * | 4/1999 | Elyasaf et al. | 356/239.8 |
| 6,131,913 | A | * | 10/2000 | Auber et al. | 277/372 |
| 6,365,425 | B1 | * | 4/2002 | Ikota et al. | 438/16 |
| 6,437,312 | B1 | * | 8/2002 | Adler et al. | 250/216 |
| 6,621,581 | B1 | * | 9/2003 | Hunt et al. | 356/601 |
| 6,774,991 | B1 | * | 8/2004 | Danko | 356/237.4 |
| 6,922,236 | B2 | * | 7/2005 | Vaez-Iravani et al. | 356/237.2 |

FOREIGN PATENT DOCUMENTS

| JP | 63184047 A | * | 7/1988 |
| JP | 11326233 A | * | 11/1999 |

* cited by examiner

*Primary Examiner*—Sang H. Nguyen
(74) *Attorney, Agent, or Firm*—Foley & Lardner LLP

(57) ABSTRACT

The invention concerns an apparatus and a method for inspection of a wafer.

The apparatus encompasses at least one stroboscopic incident-light illumination device for emitting a pulsed illuminating light beam onto a surface of the wafer and for illuminating a region on the surface of the wafer; and having [sic] at least one image acquisition device for acquiring an image of the respectively illuminated region on the surface of the wafer. The apparatus is characterized, according to the present invention, in that by at least one photodetection device for sensing light of the respective illuminating light beam, and a control device for controlling an image acquisition operation on the basis of the light sensed by the photodetection device, are provided.

Intensity fluctuations of the light flashes of the incident-light illumination device are compensated for either by normalizing image data of the illuminated region or by controlling the duration of the light flashes.

20 Claims, 4 Drawing Sheets

APPARATUS AND METHOD FOR INSPECTION OF A WAFER

CROSS REFERENCE TO RELATED APPLICATIONS

This application claims priority of the German patent application 103 59 723.9 which is incorporated by reference herein.

FIELD OF THE INVENTION

The present invention concerns an apparatus and a method for inspection of a wafer.

BACKGROUND OF THE INVENTION

In semiconductor production, wafers are sequentially processed in a plurality of process steps during the production process. With increasing integration density, demands in terms of the quality of the features configured on the wafers are rising. It is advantageous, for this purpose, if the quality of even individual process steps, for example lithography steps, can be reliably assessed during the manufacturing process and before any subsequent process step. Thus, if a determination is made, just after a process step is performed and even before a production process has been completed, that a wafer or features configured on the wafer are defective, the wafer can be immediately discarded with no need to perform additional subsequent process steps. Or wafers found to be defective can be reprocessed separately until satisfactory quality is achieved. Efficiency and yield in semiconductor production can thereby be enhanced.

Optical apparatuses are particularly suitable for inspecting the surface of wafers. Optical apparatuses are known that, by image recognition, can recognize a wide variety of features on the surface of a wafer. The wafer is usually illuminated in bright-field fashion in this context, and scanned with a camera (matrix or linear camera). In one often-used type of wafer inspection apparatus according to the existing art, the surface of the wafer is illuminated stroboscopically. A region on the surface of the wafer is illuminated by a light flash, an image of the illuminated region is acquired, and the wafer and illuminating light beam are displaced relative to one another for a subsequent image acquisition operation.

Intensity fluctuations of the light flashes used for illumination can have a disruptive effect on image evaluation accuracy in this context. For example, threshold values can be defined for image evaluation, a defect on the surface of the wafer being indicated only if those values are exceeded. Intensity fluctuations in the vicinity of the threshold value thus degrade the image evaluation accuracy. Intensity fluctuations of the light flashes used for illumination are troublesome also because they suggest imprecise operation of the wafer inspection apparatus, for example when sequentially acquired images are compared with one another.

The inventors have observed that in ordinary flash light sources, for example xenon flash lamps, flash-to-flash intensity fluctuations of approximately 5% or more can occur.

SUMMARY OF THE INVENTION

It is the object of the present invention to make available an apparatus and a method for inspection of a wafer with a stroboscopic illumination device with which, in simple and economical fashion, the influence on image acquisition accuracy of intensity fluctuations of the light flashes used for illumination can be reduced.

This object is achieved by way of an apparatus for inspection of a wafer, comprising at least one stroboscopic incident-light illumination device for emitting a pulsed illuminating light beam onto a surface of the wafer and for illuminating a region on the surface of the wafer; at least one image acquisition device for acquiring an image of the respectively illuminated region on the surface of the wafer, at least one photodetection device for sensing light of the respective illuminating light beam, and a control device for controlling an image acquisition operation on the basis of the light sensed by the photodetection device.

Additionally, the above method is accomplished by a method for inspection of a wafer, comprising the following steps:

emitting at least one pulsed illuminating light beam onto a surface of the wafer, and illuminating a respective region on the surface of the wafer;

acquiring an image of the respectively illuminated region on the surface of the wafer;

detecting the light of the respective illuminating light beam by a photodetection device, and controlling the acquisition of the image on the basis of the light sensed by the photodetection device.

Further advantageous embodiments are the subject of the internally referenced dependent claims.

The present invention makes available an apparatus for inspection of a wafer, having at least one stroboscopic incident-light illumination device for emitting onto a surface of the wafer a pulsed illuminating light beam having light flashes of a predefined duration, and for illuminating a region on the surface of the wafer with at least one of the light flashes; and having at least one image acquisition device for acquiring an image of the respectively illuminated region on the surface of the wafer. The apparatus is characterized, according to the present invention, in that at least one photodetection device for sensing light of the respective illuminating light beam is provided, as well as a control device for controlling an image acquisition operation on the basis of the light sensed by the photodetection device.

According to the present invention, the intensity of one or more illuminating light flashes is detected, and on the basis of a variable derived from that intensity, image acquisition is controlled either by normalizing acquired image data or by modifying the duration of the light flash or flashes used for illumination. With this surprisingly simple action, the influence of intensity fluctuations on image acquisition accuracy can at least be reduced with no need for complex fast control and comparison circuits, as would be the case if comparatively high flash lamp currents were being controlled. Accuracy in the detection of defects during wafer inspection can thus be enhanced in advantageously simple fashion.

The stroboscopic incident-light illumination device is preferably a flash light source, for example a xenon flash lamp, or a linear arrangement of flash light sources. The incident-light illumination device can emit substantially monochromatic light or colored light, in particular also having a quasi-continuous spectrum, in order to illuminate the surface of the wafer.

An advantageously simple apparatus can be implemented by the fact that the photodetection device is provided directly in the incident-light illumination device, since complex optical elements for imaging a portion of the light used for illumination are thus not required. For example, the photodetection device can be provided in a housing of the incident-light illumination device, for example in or in the immediate vicinity of the reflector of a flash lamp. Or the photodetection device can be provided in or on a glass-fiber illuminated field, for example on or in the immediate vicinity of a frosted glass disk that is provided in the glass-fiber illuminated field and is used to homogenize the illuminating light beam.

According to a further embodiment, a beam splitter means can be provided in a beam path of the illuminating light beam between the incident-light illumination device and the surface of the wafer, and the photodetection device can be arranged so as to detect light that is divided by the beam splitter means out of the respective illuminating light beam. In this fashion, the variable derived from the intensity of the illuminating light beam represents even more exactly the actual intensity of the illuminating light beam. That variable can be used to control image acquisition.

In a bright-field configuration, intensity fluctuations of the light flashes of the illuminating light flash are known to result in a particularly strong influence on image acquisition and evaluation. The image acquisition device is therefore arranged in a bright-field configuration.

According to a first embodiment, the control device is designed to normalize data values of the image of the illuminated region acquired by the image acquisition device to the intensity of at least one light flash sensed by the photodetection device. Normalization can be effected by suitable division or multiplication of the acquired image data values by a variable that is derived from the light of the illuminating light beam sensed by the at least one photodetection device.

Averaging can be performed over the intensity of a predetermined number of light flashes, and the data values of the image of the illuminated region acquired by the image acquisition device can be normalized to the averaged intensity.

According to a further embodiment, the control device can be designed to control the duration of the light flashes that are emitted by the respective incident-light illumination device as a function of the intensity sensed by the photodetection device. The total light energy emitted for illumination of the region on the wafer surface is thus equalized by way of a change in the duration of the light flashes.

The control device can, in this context, be designed to be sufficiently fast to control the duration of the respective light flash as a function of the intensity, sensed by the photodetection device, of the respectively current light flash. This embodiment thus controls the duration of the light flashes from one light flash to another.

The at least one photodetection device advantageously detects the light of the respective incident-light illumination device in spectrally unresolved fashion, since a particularly economical and simple wafer inspection apparatus can thus be made available. The present invention is not, however, limited thereto. In principle, the photodetection device can also detect the light of the respective incident-light illumination device in spectrally resolved fashion, in order to control the duration of the respective light flash generated by the incident-light illumination device on the basis of the spectrally resolved intensity of the light flash. For this purpose, the image data of the image of the surface of the wafer acquired in spectrally resolved fashion by the image acquisition device are preferably normalized to the respective spectral intensity of the light flash, so as thereby to compensate for intensity fluctuations in spectrally resolved fashion.

According to a further aspect of the present invention, a method for inspection of a wafer is made available having the following steps: emitting onto a surface of the wafer at least one illuminating light beam having light flashes of a predefined duration, and illuminating a respective region; and acquiring an image of the respectively illuminated region on the surface of the wafer, in which method light of the respective illuminating light beam is detected by a photodetection device, and the step of acquiring the image is controlled on the basis of the light sensed by the photodetection device.

BRIEF DESCRIPTION OF THE DRAWINGS

The invention is described below by way of example and with reference to the appended drawings, from which further features, advantages, and objects to be achieved are evident. In the drawings.

In the Figures, identical reference characters refer to identical or substantially identically functioning elements or element groups.

DETAILED DESCRIPTION OF THE INVENTION

Figure 1:
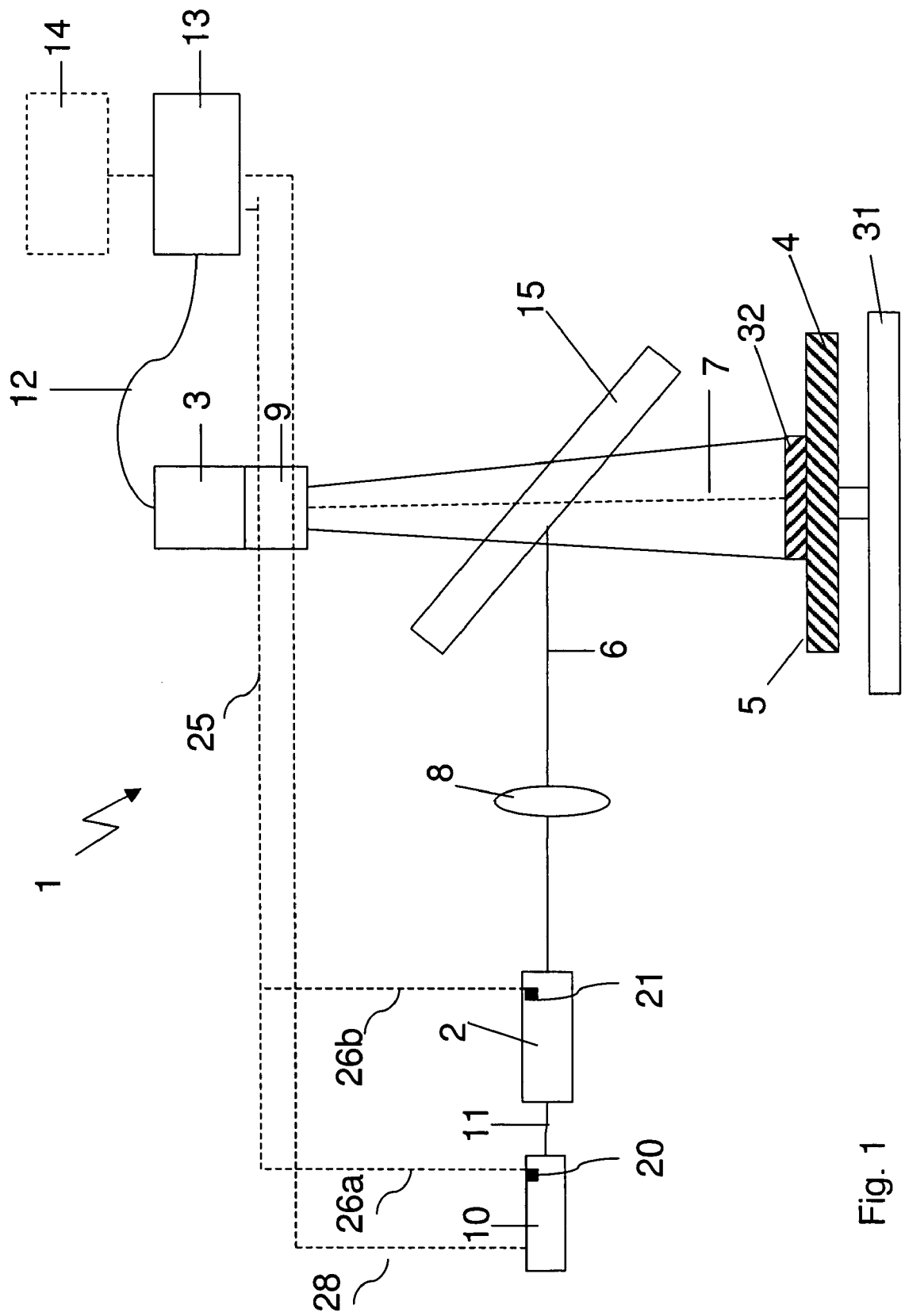
FIG. 1 is a schematic view of a wafer inspection apparatus according to a first embodiment of the present invention.

According to FIG. 1, wafer inspection apparatus 1 encompasses an incident-light illumination device 2 and a camera 3, for example a linear or CCD camera, serving as an image acquisition device. Incident-light illumination device 2 emits an illuminating light beam 6 that is reflected, by means of a schematically depicted lens 8 or an objective, from the front side of semitransparent mirror 15 onto surface 5 of wafer 4 in order to illuminate region 32 thereon, which region is depicted as being elevated only for reasons of clarity, and can encompass one or more dies on surface 5 of wafer 4. According to FIG. 1, illuminating light beam 6 is incident substantially perpendicularly onto surface 5 of wafer 4.

The light reflected from illuminated region 32 on surface 5 of wafer 4 passes through semitransparent mirror 15 and is imaged onto camera 3 with the aid of an objective 9 or a lens. Camera 3 defines an imaging axis 7 that, in the example depicted, is perpendicular to surface 5 of wafer 4 and, before semitransparent mirror 15, coincides with the beam path of illuminating light beam 6. Imaging axis 7 and illuminating light beam 6 span a plane which coincides with the drawing plane in the example depicted, and in which incident-light illumination device 2 and camera 3 are located. According to FIG. 1, camera 3 is arranged in a bright-field configuration in which the light reflected from illuminated region 32 is imaged into camera 3. In principle, however, camera 3 can also be arranged in a dark-field configuration, for example by pivoting camera 3 away from the line normal to surface 5 of wafer 4 so that only scattered light or light diffracted by surface 5 of wafer 4 is imaged into camera 3.

Wafer 4 is held on a wafer receiving apparatus 31, for example on a vacuum clamping apparatus (chuck). Wafer 4 can be held by wafer receiving apparatus 31 movably, for example rotationally movably or displaceably in two mutually orthogonal spatial directions, of which (in FIG. 1) one lies in the drawing plane and the other is perpendicular thereto.

According to FIG. 1, camera 3 is connected via a data line 12 to a computer 13, serving as a data readout device, that reads out and evaluates the acquired image data or temporarily stores them, for example for later image evaluation. Data readout device 13 is preferably a computer having a frame grabber card in order to read out the lines of a linear or CCD camera 3 periodically or in timed fashion, for example synchronously with the triggering of a flash light used for illumination of illuminated region 32 and/or synchronously with a physical displacement of wafer 4, by means of wafer receiving apparatus 31, with respect to illuminating light beam 6 and imaging axis 7, as will be described below in even further detail.

A light source (not depicted) can be provided directly in incident-light illumination device 2. As FIG. 1 schematically shows, however, incident-light illumination device 2 can also have associated with it an external light source 10 whose light is coupled into one or more light guides 11 and coupled into incident-light illumination device 2. With an embodiment of this kind, incident-light illumination device 2 can also be embodied as a glass-fiber illuminated field in order to emit a widened and comparatively homogeneous illuminating light beam 6.

A monochromatic or polychromatic light source can be used as light source 10. LEDs or LED linear arrangements driven in pulsed fashion are especially suitable as a monochromatic light source. Suitable polychromatic light sources are, in particular, flash lamps, for example xenon flash lamps; white-light LEDs; and the like. Light source 10 is preferably operated in timed fashion, for example synchronously with an image acquisition by camera 3 and/or with a displacement of wafer 4 by means of wafer receiving device 31 with respect to illuminating light beam 6 and imaging axis 7, as will be described below in even further detail.

For reasons of clarify, in FIG. 1 two possible variants are depicted together in one and the same Figure, in order to associate with illuminating light beam 6 a photodetector 20 or 21 for detecting an intensity of illuminating light beam 6. According to a first variant, photodetector 20 is arranged directly in light source 10 in order to detect the intensity of the illuminating light directly in light source 10. Photodetector 20 can, for example, be integrated into a reflector of a flash lamp housing of light source 20. Such an arrangement of photodetector 20 does not, however, allow the consideration of losses that vary with respect to time and/or space upon incoupling and/or outcoupling of illuminating light into and/or out of light guide 11 or light guide bundle 11.

According to a second variant, photodetector 21 is provided in incident-light illumination device 2. If, for example, incident-light illumination device is embodied as a glass fiber illuminated field having an associated frosted glass disk for homogenizing illuminating light beam 6, photodetector 21 can be arranged in or on the glass fiber illuminated field. The two aforementioned variants can, of course, also be combined with one another.

According to FIG. 1, photodetector 20 or 21 is connected via a signal line 26a or 26b and signal line 25 to a further signal input of data readout device 13. The signals of photodetectors 20, 21 can be transmitted to data readout device 13 in analog or digital fashion.

On the basis of the signals of photodetector 20 or 21 thus transmitted to data readout device 13, a variable is ascertained that represents an indication of the intensity of illuminating light beam 6. This variable is used, according to the present invention, to control image acquisition using computer 13 which, according to FIG. 1, simultaneously also serves as a control device, as will be described below in even further detail.

According to a first embodiment of a manner of operation for controlling image acquisition by camera 3, computer 13 ascertains the intensity of the flash light pulses of incident-light illumination device 2 on the basis of the signal detected by photodetector 20 or 21. For that purpose, the signal can be evaluated for a single light flash, for example by means of a gating circuit or an integration circuit that integrates the signal of photodetector 20 or 21 over the duration of a single light flash. Or the signal can be evaluated for a predefinable number of light flashes, for example integrated or averaged over the predefined number of light flashes. The variable thus ascertained represents an indication of the current intensity of illuminating light beam 6, and is used to normalize the image data of the image acquired by camera 3, for example by dividing the acquired image data by the variable thus ascertained. In this fashion, the image data of camera 3 are substantially no longer subject to the influence of intensity fluctuations of the light flashes of illuminating light beam 6.

According to FIG. 1, computer 13 that simultaneously also serves as a control device is connected via a control line 28 to light source 10. According to this second embodiment of a manner of operation for controlling image acquisition by camera 3, computer 13 ascertains the intensity of the flash light pulses of incident-light illumination device 2 on the basis of the signal detected by photodetector 20 or 21, as discussed above. From the variable thus ascertained, which represents an indication of the intensity of illuminating light beam 6, a control variable that is used to control light source 10 is ascertained by control device 13. In this embodiment, the duration of the light flashes used for illumination is controlled on the basis of the control variable thus ascertained, in order to compensate for intensity fluctuations of the light flashes of the illuminating light beam. The control system preferably controls the duration of a current light flash on the basis of a variable derived from the intensity of the current light flash. In principle, however, the duration of the current light flash can also be controlled on the basis of a variable derived from the intensity of one or more previous light flashes, for example in a situation in which only comparatively low-frequency intensity fluctuations are to be expected for light source 10 or incident-light illumination device 2. In this fashion, the image data of camera 3 are substantially no longer subject to the influence of intensity fluctuations of the light flashes of illuminating light beam 6.

Although a computer is depicted in FIG. 1 as the control device, according to the present invention any other control device can be used to control the duration of the light flashes. A control device of this kind can also, in principle, be arranged in or on the light source of incident-light illumination device, so that signal line 25 and control line 28 depicted in FIG. 1 can also be omitted.

Figure 2:
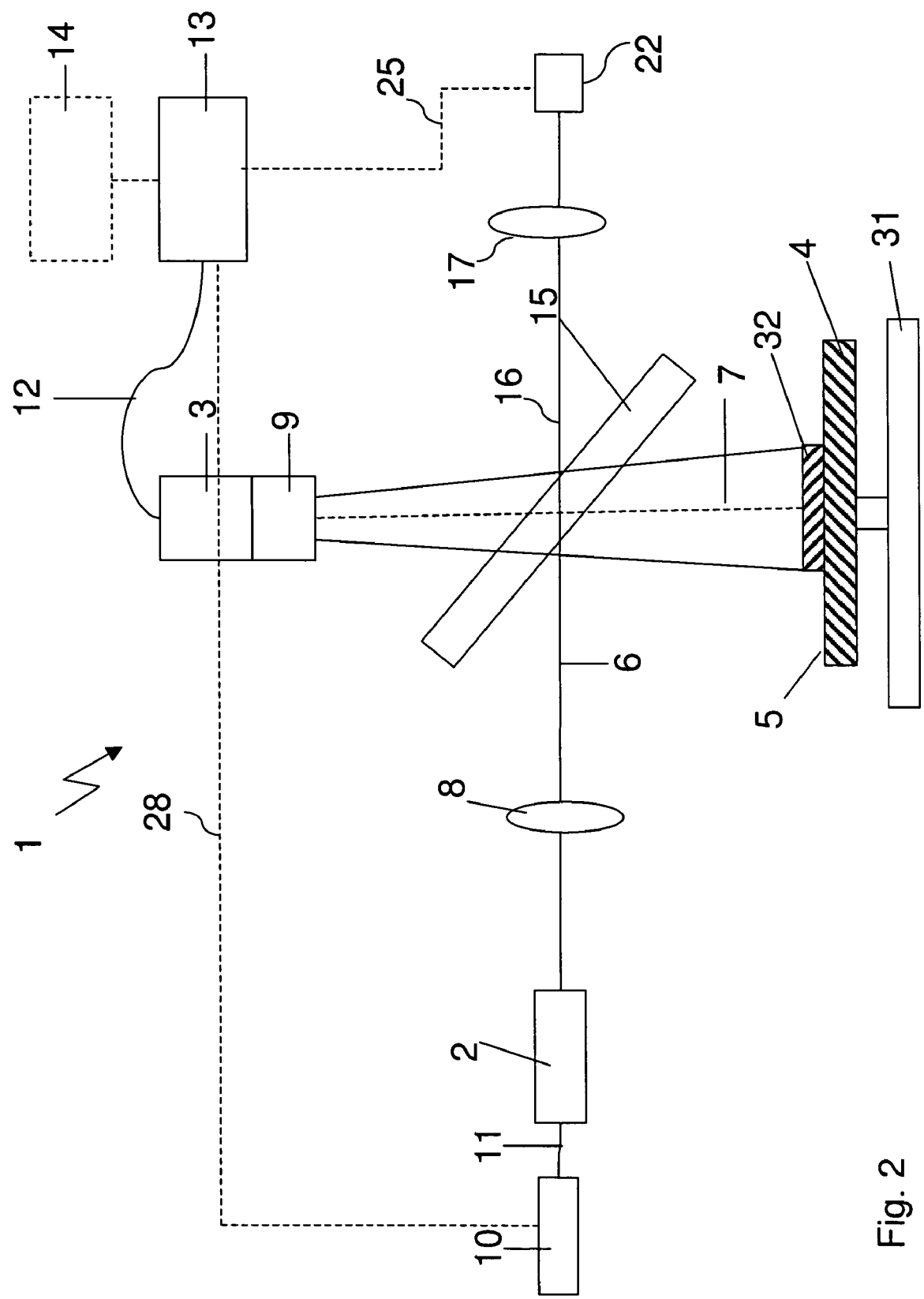
FIG. 2 is a schematic view of a wafer inspection apparatus according to a second embodiment of the present invention.

FIG. 2 shows a second embodiment of a wafer inspection apparatus according to the present invention. According to FIG. 2, sub-beam 16 of illuminating light beam 6 transmitted by semitransparent mirror 15 or by the beam splitter is imaged by means of a lens 17 onto a photodetector 22 whose output signal represents an indication of the intensity of transmitted light beam 16. According to FIG. 2, photodetector 22 is connected via signal line 25 to data readout device 13, which according to this embodiment simultaneously serves as a control device to control image acquisition by camera 3. According to the second embodiment, image acquisition by camera 3 is controlled, in the manner described above, either by normalizing the image data of camera 3 or by controlling the duration of the light flashes of light source 10 via control line 28.

As will be immediately apparent to one skilled in the art, lens 17 in front of photodetector 22 in FIG. 2 can also be omitted, or the photodetector can also detect light that is incident onto a reference surface, for example a segment of the same wafer or of a different reference wafer, and is reflected or scattered therefrom into photodetector 22.

Figure 3:
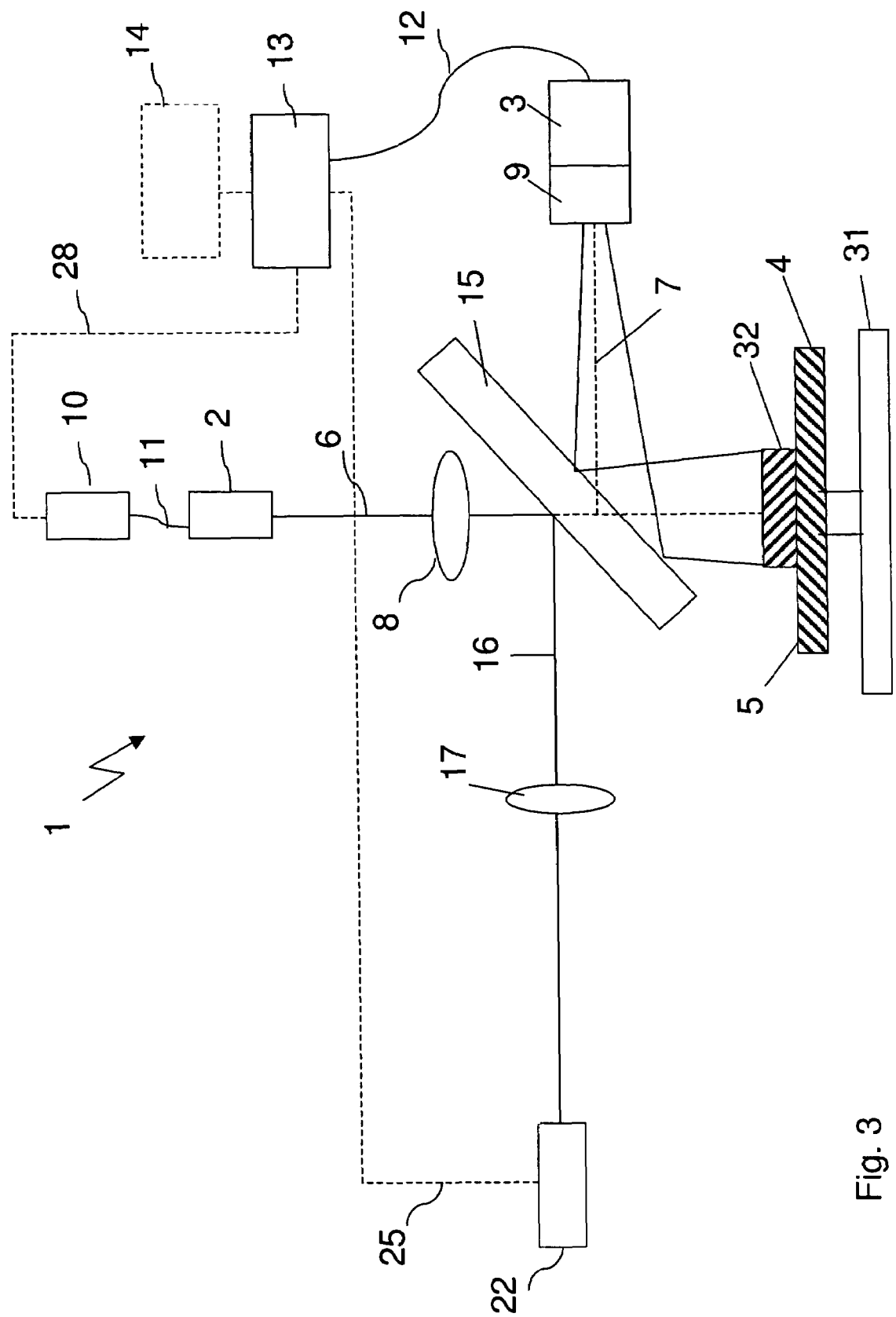
FIG. 3 is a schematic view of a wafer inspection apparatus according to a third embodiment of the present invention.

FIG. 3 shows a third embodiment of a wafer inspection apparatus according to the present invention. According to FIG. 3, incident-light illumination device 2 is arranged vertically above wafer 4, and illuminating light beam 6 is transmitted by semitransparent mirror 15 and is incident onto surface 5 of wafer 4. The light of illuminating light beam 6 reflected in illuminated region 32 is reflected at the front side of semitransparent mirror 15 onto camera 3.

According to FIG. 3, a portion of illuminating light beam 6 is reflected at the back side of semitransparent mirror 15 and is imaged through lens 17 onto photodetector 22, which is connected via signal line 25 to computer 13 that simultaneously serves as a control device. According to the third embodiment, image acquisition by camera 3 is controlled, in the manner described above, either by normalizing the image data of camera 3 or by controlling the duration of the light flashes of light source 10 via control line 28.

Figure 4:
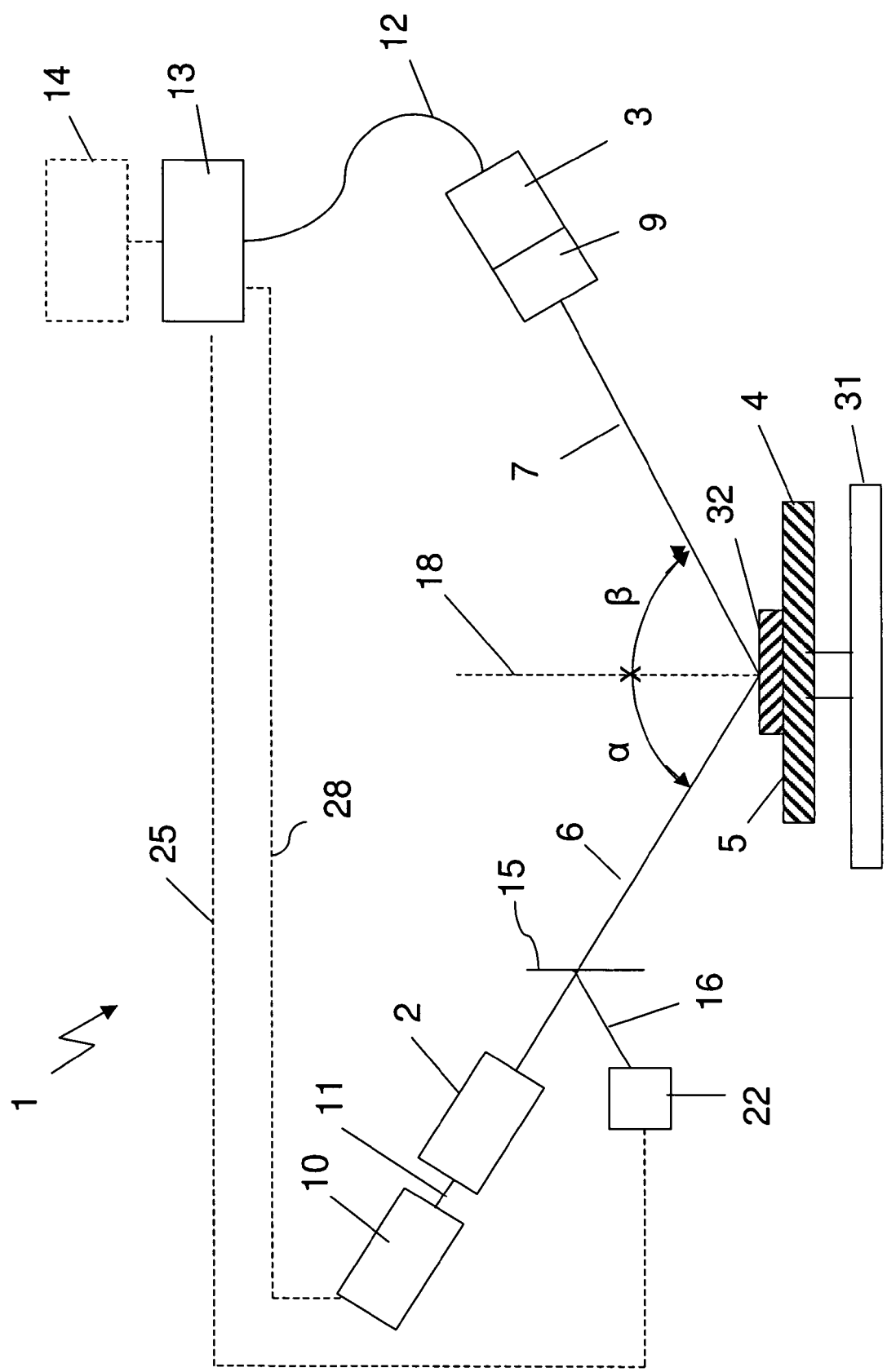
FIG. 4 is a schematic view of a wafer inspection apparatus according to a fourth embodiment of the present invention.

FIG. 4 shows a fourth embodiment of a wafer inspection apparatus according to the present invention. According to FIG. 4, illuminating light beam 6 is incident onto surface 5 of wafer 4 at an incidence angle $\alpha$. The reflected light is reflected from illuminated region 32 at an angle $\beta$ relative to line 18 normal to surface 5 of wafer 4, and imaged into camera 3.

According to FIG. 4 a beam splitter 15, for example a simple glass plate or a glass wedge, is provided in the beam path of illuminating light beam 6 and images a portion 16 of illuminating light beam 6 onto photodetector 22 that is connected via signal line 25 to computer 13 that simultaneously serves as a control device. According to the fourth embodiment, image acquisition by camera 3 is controlled, in the manner described above, either by normalizing the image data of camera 3 or by controlling the duration of the light flashes of light source 10 via control line 28.

For inspection of the surface of the wafer, the wafer is first received by the wafer receiving apparatus. This is preferably done at a predetermined orientation with respect to the wafer inspection apparatus. A wafer aligner or a comparable apparatus, which for alignment purposes can orient itself on a marking or a wafer notch, can be used to align the wafer.

A portion of the wafer, which in principle can also contain a single die but according to the present invention preferably contains several dice, is then illuminated with a light flash. The light reflected from the wafer surface is then acquired by the image acquisition device and conveyed to an image evaluation system. The wafer and illuminating light beam are then moved relative to one another, for example by rotating the wafer and/or by incremental displacement of the wafer or the illuminating light beam. A further image of the wafer surface is then acquired. Ultimately the entire surface of the wafer to be examined is scanned in this fashion.

As will be immediately evident to one skilled in the art upon examination of the description above, the incidence angle at which the illuminating light beam is incident onto the surface of the wafer can easily be varied. For that purpose, the incident-light illumination device and/or the image acquisition device can have associated with them an angular adjustment device for adjusting the incidence angle and/or return angle. The present invention also envisions, in principle, arranging the image acquisition device in a dark-field configuration. The present invention also envisions, in principle, sensing the intensity of the illuminating light beam in spectrally resolved fashion. The intensity values thus spectrally resolved can be used to normalize the image data, acquired in spectrally resolved fashion from the surface of the wafer by the image acquisition device, to the respective intensity values in spectrally resolved fashion.

What is claimed is:

1. An apparatus for inspection of a wafer, comprising at least one stroboscopic incident-light illumination device for emitting a pulsed illuminating light beam onto a surface of the wafer and for illuminating a region on the surface of the wafer; at least one image acquisition device for acquiring an image of the respectively illuminated region on the surface of the wafer, at least one photodetection device for sensing light of the respective illuminating light beam, and a control device for controlling an image acquisition operation on the basis of the light sensed by the photodetection; wherein the control device is configured to average the intensity of a predetermined number of light flashes of the illuminating light beam, and to normalize the data values of the image acquired by the image acquisition device to the averaged intensity.

2. The apparatus as defined in claim 1, wherein the incident-light illumination device encompasses a flash light source or a linear flash light source arrangement.

3. The apparatus as defined in claim 1, wherein the photodetection device is provided in the incident-light illumination device.

4. The apparatus as defined in claim 3, wherein the photodetection device is provided in a housing of the incident-light illumination device.

5. The apparatus as defined in claim 1, wherein a beam splitter is provided in a beam path of the illuminating light beam between the incident-light illumination device and the surface of the wafer, and the photodetection device is arranged so as to detect light that is divided by the beam splitter out of the respective illuminating light beam.

6. The apparatus as defined in claim 1, wherein the image acquisition device is arranged in a bright-field configuration.

7. The apparatus as defined in claim 1, wherein the control device is configured to normalize data values of the image acquired by the image acquisition device to the intensity of at least one light flash sensed by the photodetection device.

8. The apparatus as defined in claim 1, wherein the photodetection device is configured to receive light from a glass-fiber illuminated field.

9. The apparatus as defined in claim 1, wherein the control device is configured to control the duration of light flashes that are emitted by the respective incident-light illumination device as a function of the intensity sensed by the photodetection device.

10. The apparatus as defined in claim 9, wherein the control device is configured to control the duration of the respective light flash that is emitted by the respective incident-light illumination device as a function of the intensity, sensed by the photodetection device, of the respective light flash.

11. The apparatus as defined in claim 9, which is configured so that the photodetection device detects the light of the respective illuminating light beam of the respective incident-light illumination device in spectrally resolved fashion; and that image data detected in spectrally resolved fashion by the image acquisition device are normalized to the respective spectral intensity of the respective illuminating light beam.

12. A method for inspection of a wafer, comprising the following steps:
   emitting at least one pulsed illuminating light beam onto a surface of the wafer, and illuminating a respective region on the surface of the wafer;
   acquiring an image of the respectively illuminated region on the surface of the wafer;
   detecting the light of the respective illuminating light beam by a photodetection device,
   controlling the acquisition of the image on the basis of the light sensed by the photodetection device;
   averaging the intensity of a predetermined number of light flashes of the illuminating light beam; and
   normalizing the data values of the acquired image to the averaged intensity.

13. The method as defined in claim 12, wherein the light of the respective illuminating light beam is detected in a housing of an incident-light illumination device.

14. The method as defined in claim 12, wherein a beam splitter, which is arranged in a beam path of the respective illuminating light beam between an incident-light illumination device and the surface of the wafer, divides out light from the respective illuminating light beam and the divided-out light is detected, the step of acquiring the image being controlled on the basis of an intensity of the divided-out light.

15. The method as defined in claim 12, wherein the image of the illuminated region on the surface of the wafer is acquired in a bright-field arrangement.

16. The method as defined in claim 12, wherein data values of the acquired image are normalized to the intensity of at least one light flash.

17. The method as defined in claim 16, wherein the duration of light flashes that are emitted is controlled as a function of the intensity of the at least one light flash.

18. The method as defined in claim 17, wherein the duration of a respective light flash is controlled as a function of the sensed intensity of the respective light flash.

19. The method as defined in claim 12, wherein the detecting detects light from a glass-fiber illuminated field.

20. The method as defined in claim 12, wherein the light of the respective illuminating light beam is detected in spectrally resolved fashion; and wherein image data detected in spectrally resolved fashion by the image acquisition are normalized to the respective spectral intensity of the respective illuminating light beam.

* * * * *